United States Patent [19]

Dorman et al.

[11] 4,306,553

[45] Dec. 22, 1981

[54] METHOD OF MAINTAINING THE FLUIDITY OF HORMONE SOLUTIONS FOR PARENTERAL ADMINISTRATION

[75] Inventors: Frank D. Dorman; Thomas D. Rohde; Thomas G. Rublein, all of Minneapolis, Minn.

[73] Assignee: The Regents of the University of Minnesota, Minneapolis, Minn.

[21] Appl. No.: 171,091

[22] Filed: Jul. 22, 1980

[51] Int. Cl.$^3$ .............................................. A61M 5/00
[52] U.S. Cl. ............................ 128/214 R; 128/213 R
[58] Field of Search ............... 128/1 R, 213 A, 213 R, 128/214 R, 260, 214 F

[56] References Cited

U.S. PATENT DOCUMENTS

| | | | |
|---|---|---|---|
| 3,000,874 | 9/1961 | Bray et al. | 260/210 |
| 3,731,681 | 5/1973 | Blackshear | 128/214 F |
| 4,077,405 | 3/1978 | Haerten et al. | 128/213 R |
| 4,140,121 | 2/1979 | Kühl et al. | 128/213 R |
| 4,140,122 | 2/1979 | Kühl et al. | 128/213 R |

OTHER PUBLICATIONS

"The Influence of Sodium Lauryl Sulfate on the Biologic Response to the Gonadotropins and to Insulin", *J. Physiology*, Bischoff, 12-1945, vol. 145.
"The Binding of Sodium Dodecyl Sulfate to Various Proteins", *Biochem. J.*, (1968), 109,285, Rivers et al., p. 825.
"Binding of Dodecyl Sulfate to Proteins at High Binding Ratios", Proc. *National Academy Sci.*, vol. 66, No. 3, Jul. 1970, Reynolds et al.
"Effects of Ionic and Non-Ionic Detergents on Antigen-Antibody Reactions", *J. of Immunology*, vol. 119, No. 5, 11-1977, Qualtiere et al.
"The Interactions of Proteins and Synthetic Detergents", *Advances in Protein Chem.*, 1948, #4, Putnam et al., p. 79.
"The Effect of Insulin and Sodium Dodecyl Sulfate on Rat Hepatic Cell Respiration", *Advances of Biochem. & Biophysics*, 129, (1969), Tarnoff et al.

*Primary Examiner*—Robert W. Michell
*Assistant Examiner*—T. J. Wallen
*Attorney, Agent, or Firm*—Burd, Bartz & Gutenkauf

[57] ABSTRACT

A method of preventing the precipitation of hormone preparations within drug delivery systems that depend on the fluidity of the infusate for proper function. A non-toxic water soluble detergent is dissolved in the hormone solution prior to the introduction of the solution into the drug delivery system. The detergent is added in amount sufficient to prevent precipitation of the hormone during long-term storage in the drug delivery device. According to one form of usage, the hormone-detergent solution is charged to the pressurized drug storage chamber of an implanted infusion pump by injection through the patient's skin. As the solution is discharged from the delivery device by the constant pressure exerted upon the storage chamber, its low rate of flow is controlled by a restricted fluid passage. The solution is conveyed to an infusion site and diluted by the blood stream.

14 Claims, No Drawings

METHOD OF MAINTAINING THE FLUIDITY OF HORMONE SOLUTIONS FOR PARENTERAL ADMINISTRATION

The Government has rights in this invention pursuant to Contract No. NO 1-AM-8-2217 awarded by the National Institutes of Health.

BACKGROUND OF THE INVENTION

1. Field of the Invention

This invention relates to a method of preventing the precipitation of hormone preparations within drug delivery systems that depend on the fluidity of the infusate for proper function. One system of this type is the implantable infusion pump illustrated and described in Blackshear et al U.S. Pat. No. 3,731,681, the disclosure of which is incorporated herein by reference. The addition of specific detergents in low concentrations increases the solubility of the hormone, such as insulin, in water without affecting its biological activity. The detergent solubilizes both native or denatured hormones and inhibits the action of precipitation agents, such as metal ions.

The control of many cellular functions in an organism is via hormones, such as insulin, human growth hormone, glucagon, and the like, secreted in very small amounts by specific glands into the blood stream. These hormones have high affinity for specific sites on or in the membranes of the specific cells. The hormones are typically small proteins with a marginal solubility in blood. The hormone is functionally active in the hydrophobic lipid membrane. A typical hormone deficiency disease is diabetes where the beta cells in the pancreas have been destroyed and the medical treatment is the administration of insulin from animal origins.

Recent studies have suggested that management of blood glucose in insulin dependent diabetics can be improved by administering insulin by pump on a continuous basis, or in pulses several minutes apart, rather than by intermittent injections as is now common practice. One factor limiting the length of time this kind of administration can be maintained is precipitation of insulin in the flow passages of these pumps causing flow stoppage. There is mounting evidence that such improvement of control, if provided on a long-term basis, might inhibit or alleviate the development of diabetic complications such as blindness and kidney failure. Thus, the availability of an agent to maintain the solubility of insulin under those circumstances could potentially have substantial impact on the treatment of diabetes.

The implanted infusion pump of U.S. Pat. No. 3,731,681 has been used successfully to administer heparin for the treatment of blood clotting disorders. Heparin is a highly soluble and very negatively charged molecule. No difficulty was encountered with the metering of this drug using small bore capillary tubes or with the delivery of the drug to the blood stream using a conventional silicone rubber catheter. Over five years of continuous intravenous heparin delivery has been achieved in dogs with this system. Comparable infusion time periods were achieved when sterile water was substituted for heparin. However, when the same pump was used to deliver commercial regular insulin, in standard insulin diluting fluid, the pumps would flow normally for only one to two months. A progressive blockage of the passageways took place with eventual flow stoppage. Often a solid plug of amorphous proteinaceous material was found at the distal end of the small bore capillary, but plugs were found in some cases in the proximal end of the capillary or in the larger bore cannula. These plugs were dissimilar from thrombus plugs which sometimes occurred at the cannula tip.

The major difficulty in the administration of insulin chronically by implanted infusion pump comes from the nature of proteins and the very dilute solution needed. Since insulin delivered by injection is normally administered rapidly (either intramuscularly or intravenously), there is no problem with any possible precipitation reaction with the blood. When the insulin is given chronically, the flow rate by necessity becomes low. This permits insulin and blood components to react in and plug the end of the catheter.

Others using chronic insulin delivery systems have experienced similar problems. Long-term functioning of insulin delivery systems cannot be maintained using standard insulin preparations. The initial approach was to solve the problem of plugging by hardware changes. When these proved to be ineffective, the next approach was to alter the solution used to solubilize the insulin.

2. Prior Art

F. Bischoff (The influence of sodium lauryl sulfate on the biologic response to the gonadatropins and to insulin. Amer. J. of Physiology 145: 123–129, 1945) discloses that if a solution of sodium lauryl sulfate (sodium dodecyl sulfate) (SDS) and insulin is diluted to 0.12% SDS before delivery, no loss in activity of the insulin was found. Although the insulin is denatured by high SDS concentration (1 to 5%) and would be partially destroyed in the blood stream, the insulin can return to its natural state rapidly when diluted and function normally. SDS was not useful as a solubilizing agent for insulin when given by conventional subcutaneous injections since the insulin is partially destroyed before it can be absorbed into the blood stream.

It is known that the binding of detergents to proteins occurs readily. The binding ratio for the common anionic detergent sodium dodecyl sulfate has been determined for proteins to be: 0.4 gm–1.4 gm SDS/gm protein (Rosalind Pitt-Rivers and F.S.A. Impiombato. The binding of sodium dodecyl sulfate to various proteins. Biochem Journal 109:825–830, 1968, and Jacqueline Reynolds and Charles Tanford. Binding of dodecyl sulphate to proteins at high binding ratios. Proceedings of the National Academy of Sciences. 66:1002–1007, 1970).

SDS is also reported to disrupt or prevent the formation of antigen-antibody complexes (Louis Qualtiere, Amil Anderson, and Paul Meyers. Effects of ionic and nonionic detergents on antigen-antibody reactions. J. of Immunology 119:1645–1651, 1977).

Bray et al U.S. Pat. No. 3,000,874 discloses that, although it is not used as a drug by itself, SDS is used to enhance absorption of other drugs.

SUMMARY OF THE INVENTION

Broadly stated, this invention is directed to a method of maintaining the fluidity of hormone solutions for parenteral administration at a low flow rate to a chronically ill patient suffering from a hormone-deficiency disease from an implanted pressure actuated drug delivery device without loss of biological activity. A nontoxic water soluble detergent is dissolved in the hormone solution prior to the injection of the solution into the drug storage chamber of the delivery device, for thorough dissolution and uniform distribution through the solution. The detergent is added in a small but effective amount sufficient to prevent precipitation of the hormone during long-term storage in the drug delivery device of up to several weeks. Thereafter, the hormone-detergent solution is charged to the drug storage chamber by injection through the patient's skin. As the solution is discharged from the delivery device by the constant pressure exerted upon the storage chamber, its low rate of flow is controlled by a restricted fluid passage. The solution is conveyed to an infusion site by tubular passage means, such as a small diameter catheter.

DETAILED DESCRIPTION OF THE PREFERRED EMBODIMENT

According to the invention, a standard injectable hormone solution is admixed with a water soluble detergent comprised of an alkali metal salt of an alkyl sulfate in the amount of about 0.1 to 5% by weight, sufficient to prevent precipitation of the hormone after charging into the drug storage chamber of a pressure actuated drug delivery device, such as the infusion pump of U.S. Pat. No. 3,731,681. The detergents are prepared by sulfation and neutralization of aliphatic alcohols in the range of 8 to 16 carbon atoms, including staight and branched chains, both saturated and unsaturated. Exemplary detergents, commercially available in medicinal grades, include sodium dodecyl sulfate (SDS) and sodium tetradecyl sulfate (STS). The detergent is added in amount to produce a detergent to hormone mole ratio of at least between 12 to 1 and 80 to 1. Excess detergent forms a protective micelle around the hormone molecules when their hydrophobic bonds are broken by the detergent. In addition, the surfactant properties of the detergent reduce the surface tension between the hormone and the surfaces of components of the drug delivery system.

The hormone-detergent solution is injected into the drug storage chamber of the drug delivery device of a patient suffering from a hormone-deficiency disease. From the storage chamber the solution is discharged through a fluid restrictor at a low flow rate of from about 1 cc to 15 cc per day, depending upon the needs of the patient, and passed into the blood stream at the desired infusion site. Upon passage into the blood stream, the solution is immediately diluted to below about 0.15% by weight to rapidly return the hormone to its normal state where it may function normally with no loss of activity.

Experimental work in connection with the invention was conducted with insulin and SDS. After deciding to use SDS as a solubilization and fluidization agent, experiments were performed according to the following examples to determine:

1. The minimum SDS concentration needed that would prevent insulin precipitation from pH or metal ions at blood concentration.
2. The effectiveness of insulin when solubilized with SDS.
3. The ability of SDS to prevent insulin precipitation in pumps when used in-vivo.
4. Any toxic effect from SDS at the concentration used.

EXAMPLE 1

SDS concentration needed

A method was developed to test the ability of the SDS/insulin complex in preventing precipitation. A protein is least soluble at its isoelectric point. At this pH there is no net charge on the protein, thus, the molecules no longer repel each other but are attracted to form insoluble precipitates. The isoelectric point of insulin was determined in distilled water to be pH 5.4. Samples of beef-porcine insulin containing 10 u/ml were prepared. The volume of each sample was kept constant at 10 ml. The pH of each vial was adjusted using 0.1 m HCL to approximately pH 5.4 (5.3–5.5). The appearance of each solution and ending pH were recorded. The data are summarized in Table I. Additional groups of samples containing 25 u/ml and 50 u/ml in various percentages of SDS were prepared. The pH was adjusted to approximately pH 5.4 the appearance and ending pH recorded. In each group some of the samples became cloudy; others remained clear. Whereas a solution containing 10 u/ml in 0.025% SDS was clear, a sample of 25 u/ml in 0.025% SDS was cloudy. However, the 25 u/ml sample in 0.075% SDS was clear. In order to compare these findings the number of moles of SDS and insulin in each solution was calculated. These calculations revealed that at approximately a 12/1 ratio, moles SDS/moles insulin the solution remained clear even at pH 5.4. To further test this ratio, a group of samples containing 15 u/ml insulin in various SDS solutions was prepared; again, at a ratio approximately 12/1, the solutions cleared. Solutions above this ratio also remained clear. In an attempt to further elucidate the precipitation at the isoelectric point, the experiment was carried out using a spectrophotometer to assess precipitate formation. At 340 NM the instrument was zeroed with insulin/SDS solutions at a neutral pH. The pH was adjusted to approximately 5.4 and the samples read for optical density. This experiment revealed a slightly higher ratio, approximately 20/1 necessary for clearing. The gm/gm ratio of this combination is well within the limits of known binding of detergents to proteins.

Another test was devised to assess ability of SDS to prevent precipitation. It is known that both zinc and copper can precipitate insulin from solution and form crystals. The insulin solutions used already contain some zinc, however, not enough to crystalize the molecule.

| Solution Insulin/SDS | Beginning pH | Ending pH | Appearance | Molecular Ratio | Optical Density |
|---|---|---|---|---|---|
| 10 μ/ml | | | | | |
| .015% | 7.4 | 5.3 | Cloudy | 7.67/1 | |
| .020% | 7.6 | 5.4 | Cloudy | 10.33/1 | .300 |
| .025% | 7.8 | 5.4 | Clear | 12.98/1 | .05 |
| .050% | — | 5.45 | Clear | 22.5/1 | .002 |
| 15 μ/ml | | | | | |
| .025% | 7.6 | 5.3 | Cloudy | 7/1 | |
| .04% | 7.7 | 5.3 | Clear | 11.3/1 | |
| .05% | 7.8 | 5.2 | Clear | 14.6/1 | |
| 25 μ/ml | | | | | |
| .025% | 7.8 | 5.4 | Cloudy | 3.82/1 | |
| .050% | 7.8 | 5.4 | Cloudy | 7.46/1 | |
| .075% | 6.8 | 5.4 | Clear | 11.46/1 | .02 |
| .125% | — | 5.4 | Clear | 18.7/1 | .007 |
| 50 μ/ml | | | | | |
| .075% | 7.8 | 5.3 | Cloudy | | |
| .1% | 7.8 | 5.4 | Cloudy | 5/1 | |
| .125% | 7.8 | 5.4 | Cloudy | 6.2/1 | |
| .150% | 7.8 | 5.2 | Cloudy | 7.5/1 | |
| .200% | 7.8 | 5.3 | Slightly Cloudy | 10/1 | .012 |
| .3% | — | 5.4 | Clear | 15/1 | .01 |

-continued

| Solution Insulin/SDS | Beginning pH | Ending pH | Appearance | Molecular Ratio | Optical Density |
|---|---|---|---|---|---|
| .4% | — | 5.4 | Clear | 20/1 | .005 |

It is speculated that metal ions present in the mammalian system could be free to react with insulin to cause a precipitate. Copper is present in vivo at levels near 150 μg/100 ml. It is not known how much of this ion would be available to react with insulin. The assumption was made that potentially all of the ion would be. A modification of the pH stability test was devised. Samples of insulin in various percents SDS were prepared. In place of pH adjustment, 3.5 ml of a copper solution (0.005 m) containing 1.1 mg was added to the vials. It was determined that a mole ratio of 80/1 would be necessary to prevent precipitation. The end points in this experiment, however, were not as sharp as those of the pH stability.

EXAMPLE 2

Insulin activity and SDS solutions

It has been reported that an insulin/SDS complex would dissociate when introduced into the blood system. (Putnam, F. W. The interaction of proteins and synthetic detergents. Advances in Protein Chemistry 4:79–122, 1948) and that insulin in the presence of SDS had an increased bioactivity (J. Tarnoff and H. R. Strausser. The effect of insulin and sodium dodecyl sulfate on rat hepatic cell respiration. Archives of Biochemistry and Biophysics 129:273–276, 1969). An experiment was designed to show that, if activity is retained, then the vital structure must likewise remain intact. This in-vivo insulin activity test is a qualitative method of evaluating an insulin preparation via its ability to lower blood glucose.

Two solutions were compared. They were U-4 neutral regular insulin diluted with 1% SDS (solution "A") and U-4 neutral regular insulin diluted with neutral regular insulin diluting fluid (solution "B"). They were both stored at 37° C. in an air incubator. Once or twice weekly, for 8 weeks, the insulin solutions were tested in dogs previously made diabetic with alloxan. Each test required two consecutive days. On the first day solution "A" was tested and on the following day solution "B" was tested. For each test the procedure was as follows:
1. A baseline 1 ml whole blood sample was taken.
2. At t=0, a 4 unit injection of the appropriate insulin solution was given.
3. 1 ml whole blood samples were then taken at t=5 min and at t=15 min.
4. Dextrostix ®-Ames ® meter determinations were made of each sample for blood glucose levels.

A decrease of blood glucose indicates that the insulin has activity and no change in the blood glucose level would indicate that the insulin has little or no activity.

The data gathered over the eight week period led to the conclusion that the activity of SDS/insulin is retained and not different from that of regular insulin under the same conditions. It is hypothesized that if the activity remains, the vital structure is intact. In addition, one diabetic dog has been maintained solely on insulin in SDS for 2½ months from an implanted pump.

EXAMPLE 3

Effectiveness in Preventing Plugging

A comparison was made between the flow rate of insulin delivered by pumps implanted in dogs. The tests were run in each case until the pump stopped flowing. The flow rate was determined by the weekly refill volume needed. Some pumps were run with insulin in Standard Insulin diluting fluid and some with insulin in a 1% SDS solution. Where Standard Insulin diluting fluid is used, the pump flow rate starts to drop immediately and goes to zero in an average of 40 days. In contrast, when the insulin included SDS, the flow has remained constant out to 280 days to date. None of the pumps using SDS solution have plugged due to insulin precipitation in the capillaries in the tests to-date. Although insulin solutions were found to change in pH during storage in the pump and also during delivery, the pH stayed well within the soluble zone above pH 6.4 up to the blood pH of 7.4 at the exit of the catheter.

EXAMPLE 4

SDS Toxicity

A literature search was made on the physiological effects of detergents. SDS has a $LD_{50}$ of 1288 mg/kg when given orally in rats, and has a $LD_{50}$ of 118 mg/kg when given I.V. to rats and mice. SDS is metabolized rapidly by the same route as the natural body detergent-like substances (e.g. free fatty acids). The half life in the body is about one day.

For insulin solutions of the concentrations expected to be used in the pump (50–75 units/cc) for clinical applications the SDS concentration needed to ensure solubility of insulin at its isoelectric point is 0.30% by weight. However, when mixed with solutions that contain normal $Zn++$ and $Cu++$ ion concentrations found in the plasma a concentration of 1% SDS is needed for solubility. The dose rate of 1 cc/day of the (50–75 unit/cc) insulin would thus give a dose to a 70 kg human of: $1.43 \times 10^{-4}$ gm/kg. This is 826 times smaller than the estimated intravenous $LD_{50}$ dose assuming a mean half life of one day.

Insulin in 1% SDS solutions have been given intravenously at a flow rate of 1 cc/day continuously for 7 to 10 months to date in 4 dogs with no manifest ill effects.

In summary, the results demonstrate that SDS significantly extends the useful use period of an implanted hormone infusion pump. The use of a detergent as an additive serves several functions:
1. The insulin and other hormones are solubilized without damage.
2. Denatured insulin that would otherwise precipitate is held in solution.
3. Metal ions from the insulin, the pump or the blood stream are held in solution.
4. Small particles are suspended and if small enough will pass out the filter and capillary.
5. Filter and capillary surfaces are wetted to eliminate air blocks.
6. The detergent is a weak bacteriostatic agent.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A method of maintaining the fluidity of hormone solutions for parenteral administration at a low flow rate to a chronically ill patient suffering from a hormone-deficiency disease from a drug delivery device that depends on the fluidity of the infusate for proper functioning, without loss of biological activity, which method comprises:
   (A) dissolving a small but effective amount, sufficient to prevent precipitation of the hormone, of a non-toxic water soluble detergent in the hormone solution prior to injection into the drug storage chamber of the delivery device, and
   (B) charging the drug storage chamber of the drug delivery device with said hormone-detergent solution.

2. A method according to claim 1 wherein said detergent is present in amount between about 0.1 and 5% by weight and at least about 12/1 to 80/1 mole ratio of detergent to hormone.

3. A method according to claim 1 wherein said hormone is insulin.

4. A method according to claim 1 wherein said detergent is an alkali metal salt of a straight chain aliphatic sulfate in the range from 8 to 16 carbon atoms.

5. A method according to claim 4 wherein said detergent is sodium dodecyl sulfate.

6. A method according to claim 1 wherein the pH of the hormone-detergent solution is between the isoelectric point of the hormone of about 5.3 and blood pH of about 7.4.

7. A method according to claim 1 wherein said drug delivery device is an implanted pressure actuated device whose storage chamber is charged by injection of the hormone-detergent solution through the skin of the patient.

8. A method of aldministering a hormone solution at a low flow rate to a chronically ill patient suffering from a hormone-deficiency disease, which method comprises:
   (A) dissolving a small but effective amount, sufficient to prevent precipitation of the hormone, of a non-toxic water soluble detergent in the hormone solution to maintain the fluidity of the solution without loss of biological activity,
   (B) charging the drug storage chamber of a drug delivery device that depends on the fluidity of the infusate for proper functioning with the hormone-detergent solution,
   (C) continuously discharging the solution from the storage chamber through a restricted flow passage into the blood stream of the patient at a rate between about 1 and 15 cc solution per day, and
   (D) diluting the solution with the blood stream as it enters the blood stream.

9. A method according to claim 8 wherein said detergent is present in amount between about 0.1 and 5% by weight and at least about 12/1 to 80/1 mole ratio of detergent to hormone.

10. A method according to claim 8 wherein said hormone is insulin.

11. A method according to claim 8 wherein said detergent is an alkali metal salt of a straight chain aliphatic sulfate in the range of 8 to 16 carbon atoms.

12. A method according to claim 11 wherein said detergent is sodium dodecyl sulfate.

13. A method according to claim 8 wherein the pH of the hormone-detergent solution is between the isoelectric point of the hormone of about 5.3 and blood pH of about 7.4.

14. A method according to claim 8 wherein said drug delivery device is an implanted pressure actuated device whose storage chamber is charged by injection of the hormone-detergent solution through the skin of the patient.

* * * * *

UNITED STATES PATENT AND TRADEMARK OFFICE
CERTIFICATE OF CORRECTION

PATENT NO. : 4,306,553

DATED : December 22, 1981

INVENTOR(S) : Frank D. Dorman et al

It is certified that error appears in the above-identified patent and that said Letters Patent are hereby corrected as shown below:

Column 8, line 1, "aldministering" should be --administering--.

Signed and Sealed this

Twenty-eighth Day of December 1982

[SEAL]

Attest:

GERALD J. MOSSINGHOFF

Attesting Officer     Commissioner of Patents and Trademarks